United States Patent [19]

Pratt, Jr. et al.

[11] Patent Number: 4,791,656
[45] Date of Patent: Dec. 13, 1988

[54] ONE-BLOCK CALIBRATION METHOD FOR DENSITY GAUGES

[75] Inventors: James D. Pratt, Jr., Raleigh; Ralph L. Ely, Jr., Durham, both of N.C.

[73] Assignee: Troxler Electronic Laboratories, Inc., Research Triangle Park, N.C.

[21] Appl. No.: 39,629

[22] Filed: Apr. 16, 1987

[51] Int. Cl.⁴ .............................................. G06F 15/52
[52] U.S. Cl. ...................................... 378/89; 378/207; 364/571.02; 250/252.1
[58] Field of Search .................... 378/89.207; 250/308, 250/252.1; 364/571, 414

[56] References Cited

U.S. PATENT DOCUMENTS

| | | | |
|---|---|---|---|
| 3,334,230 | 8/1967 | Shaffer | 250/252.1 |
| 3,348,046 | 10/1967 | Lloyd | |
| 3,668,401 | 6/1972 | Shah et al. | |
| 3,742,217 | 6/1973 | Eakman et al. | |
| 4,152,600 | 5/1979 | Berry | 250/252.1 |
| 4,155,009 | 5/1979 | Lieber et al. | 250/308 |
| 4,577,338 | 3/1986 | Takahashi et al. | 378/207 |
| 4,587,623 | 5/1986 | Regimand et al. | 250/252.1 |

Primary Examiner—Carolyn E. Fields
Assistant Examiner—Joseph A. Hynds
Attorney, Agent, or Firm—Bell, Seltzer, Park & Gibson

[57] ABSTRACT

Nuclear density gauges of the type having a gamma source which is positionable at several different source depth positions with respect to a detector are calibrated in an efficient and advantageous manner by a calibration procedure which reduces the number of experimental counts which must be taken. In accordance with the present invention, a single calibration block is employed and counts are taken at one or more source depth positions on the block. Through the use of historically derived relationships between the count rate obtained from the calibration block to the count rates obtained from at least two different calibration blocks of other known densities, the expected calibration counting rates for the other blocks can be obtained. These calculated counting rates are then used along with the experimentally determined counting rate to obtain the calibration constants for the gauge.

6 Claims, 1 Drawing Sheet

ONE-BLOCK CALIBRATION METHOD FOR DENSITY GAUGES

FIELD AND BACKGROUND OF THE INVENTION

The present invention relates to the calibration of nuclear density gauges, and more particularly, relates to an improved method of initially calibrating such gauges.

Nuclear radiation gauges for determining density characteristics of soil and asphaltic materials are well known. One example of such a gauge is described in U.S. Pat. No. 2,781,453. Such gauges employ the phenomenon of Compton scattering of gamma rays and are well known to those skilled in the art as "scatter" gauges.

Nuclear density gauges currently in use, for example the Troxler Model 3400 and 4400 series gauges manufactured by the assignee of the instant invention, employ a nuclear source that emits gamma radiation into the test specimen and a detector system for measuring the scattered radiation. The gauge is designed to operate both in a "backscatter" mode and in a "direct transmission" mode, and for this purpose, the source is vertically movable from a "backscatter" position where it resides within the gauge housing to a series of "direct transmission" positions where it is inserted at selected depths into bores in the test specimen.

The counts received by the detector system are found to be related to the density of the scattering medium by an expression of the following form $$CR = A\ exp(-BD) + C,$$

where:
CR = count ratio (the accumulated count normalized to a reference standard count
D = density of test specimen, and
A, B and C are constants.

The gauges are factory calibrated to arrive at values for constants A, B, C for each gauge. The factory calibration procedure which has been used in the past is a time-consuming iterative process which may require several hours to complete. In order to determine values for the three calibration parameters A, B, and C of the above equation, count measurements must be taken on at least three materials of different densities at each source position. In some instances, as many as five calibration standards have been employed in order to take into account the mass attenuation coefficients of different soils. Thus, a large number of individual counts must be taken. For example, for a gauge having a 12 inch source rod with seven different source depth positions, a minimum of 21 separate counts must be taken when three calibration blocks are used. Each count is taken for a period of time, for example, four minutes, with longer periods of time producing greater precision. Once all of the counts are taken, then values for the calibration parameters A, B, and C at each source depth position are calculated. It will thus be seen that this calibration process is a time-consuming and labor intensive procedure.

SUMMARY OF THE INVENTION

The present invention overcomes the disadvantages noted above by providing a significantly less time-consuming calibration procedure which is applicable for calibrating gauges of identical construction. In addition to providing a reduction in time and attendant labor costs, the calibration procedure of the present invention is as accurate as the prior calibration methods.

In accordance with the present invention, a single calibration block is employed and counts are taken at one or more source depth positions on the block. Through the use of historically derived relationships between the count rate obtained from the calibration block and the count rates obtained from at least two different calibration blocks of other known densities, the expected calibration counting rates for the at least two additional blocks can be obtained. These counting rates are then used in the normal fashion to obtain the calibration constants A, B, and C.

Thus, the present invention in one aspect provides a method of calibrating a nuclear density gauge of the type having a gamma source which is positionable at several different source depth positions with respect to a detector to obtain the calibration constants A, B and C of the exponential equation $$CR = A\ exp(-BD) + C$$

where:
CR is the count ratio derived by comparing an accumulated count from a test specimen to a standard count,
D is the density of the test specimen, and
A, B and C are calibration constants
wherein the method is characterized by reducing the number of experimental count readings required for calibration, and comprises the steps of:

(a) positioning the source at a predetermined source depth position on or in a calibration block of known density and obtaining a count by the detector for a predetermined period of time;

(b) calculating at least one additional count at another known density or another known source depth position using historically derived relationships between the count obtained from said calibration block of known density and the counts obtained from calibration blocks of other known densities and other known source depth positions; and (c) utilizing the experimental count obtained from step (a) and the calculated count obtained from step (b), together with the respective densities, to derive a set of calibration constants A, B and C.

In accordance with a further aspect of the present invention, it is possible to calculate the count rates at other source depths from a single experimental count. In this procedure, a single count is taken at an intermediate depth on the single calibration block, and using historically derived relationships of the counts at other depths in the same block, the expected counting rate can be determined for the other depths. The calibration procedure described above is then used to calculate additional counts at other known densities, and to thereby obtain a sufficient number of counts to complete the calibration and determine the constants A, B, and C at each depth.

The success of these calibration methods depends upon the degree to which gauge geometry is reproduced from gauge to gauge. Given reproducible geometry from gauge to gauge, a significant advantage of the above methods, aside from the savings in calibration time, is reduction of the variation in the counts normally expected from an experimental determination of each count.

BRIEF DESCRIPTION OF THE DRAWINGS

The invention will be more fully understood from the detailed description which follows, when taken in connection with the accompanying drawings, in which.

DESCRIPTION OF THE ILLUSTRATED EMBODIMENT

While the present invention will be described hereinafter with particular reference to the accompanying drawings, it is to be understood at the outset that it is contemplated that the present invention may be varied in specific detail from that illustrated and described herein while still achieving the desirable characteristics and features of the present invention. Accordingly, the description which follows is intended to be understood as a broad enabling disclosure directed to persons skilled in the applicable arts, and is not to be understood as restrictive.

Figure 1:
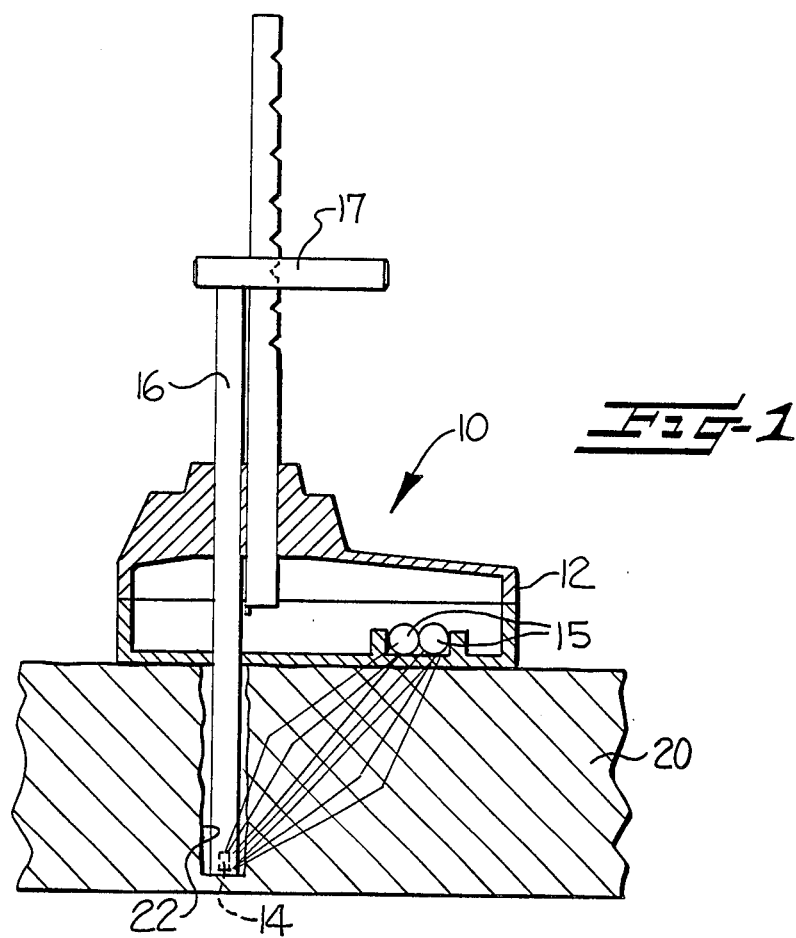
FIG. 1 is a cross-sectional view of a nuclear density gauge positioned on a calibration block at a particular depth for carrying out the calibration procedure of the present invention.

Referring now more particularly to the drawings, in FIG. 1 a nuclear density gauge is indicated by the reference character 10 positioned on the surface of a calibration block 20. The gauge 10 includes a housing 12, a source of radiation 14, and a radiation detector 15. The radiation source may be a Cs-137 source of gamma radiation and the detector may take the form of Geiger-Muller tubes sensitive to photons. The source is mounted at the end of a vertically movable probe rod 16. By means of a handle 17, the source 14 is movable from a safe position (not shown) where the source is fully withdrawn within the housing 12, to a backscatter position where the source is positioned adjacent the lower surface of the housing, and to each of several direct transmission positions in which the source rod projects a predetermined distance beneath the housing. Typically gauges of this type provide for several direct transmission positions ranging from about 2 inches to about 12 inches in depth.

With the source rod 16 positioned in the direct transmission mode as shown in FIG. 1, the source 14 is located at a selected depth position within a bore 22 formed in the calibration block 20 and directly transmits photons along random paths to the detector as shown schematically in the drawing.

In obtaining a density measurement, the following working exponential equation (or an equivalent form) is utilized:

$$CR = A \exp(-BD) + C$$

where:

CR is the count ratio derived by comparing an accumulated count from a test specimen to a standard count, D is the density of the test specimen, and A, B and C are calibration constants.

In order to convert the experimental count ratio into a density reading, the gauge must be initially calibrated to obtain values for the constants A, B, and C at each source depth position. (As used herein the term "source depth position" includes each relevant direct transmission source depth position of the gauge, as well as the source position in the backscatter mode.) As noted above, in connection with the description of the prior art, the prior conventional procedure for calibrating the gauge has been carried out by taking experimental readings of the count ratio on calibration blocks of known densities. Since there are three unknowns (A, B and C), then experimental readings must be obtained from at least three calibration standards of known densities (for example, magnesium, aluminum, and a standard of intermediate density such as a laminated magnesium-/aluminum block). The count rates derived from the tests are normalized to a reference standard count and expressed as "count ratios". The count ratios are then related to the densities of the three blocks by an exponential equation in the form noted above.

The nuclear density gauge 10 includes an associated memory device (for example a PROM) for storing the three constants A, B, and C for each source depth position. Thus, for example, a gauge having seven source depth positions (one backscatter and six direct transmission positions) would have seven sets of constants A, B, and C for a total of 21 constant values stored in the PROM. It will thus be seen that a large number of experimental counts must be taken in order to calculate the calibration constants A, B, and C for each source depth position by conventional calibration procedures.

The present invention significantly reduces the number of necessary experimental readings by providing a procedure by which given at least one experimental reading at a known source depth position and known density, expected values at other source depth positions and other densities can be calculated utilizing historically derived relationships between the experimental counts obtained from the calibration block of known density to the counts previously obtained from calibration blocks of other known densities and other known source depth positions. In this procedure, one experimental point is sufficient and necessary to calculate the expected counts for the remaining source depth positions and densities. More than one experimental reading can be utilized, and may provide more accurate data in some applications; however, such additional data points are not essential.

The calibration procedure of this invention is applicable for calibrating gauges which are of identical construction, and assumes that the gauges are manufactured with a reproducible source-detector geometry. For a particular style or model of gauge, historically derived relationships between the count readings obtained at various source depth positions and with calibration blocks of various known densities are determined experimentally. Using the experimental data, equations are developed interrelating the count rate at a given source depth position and density to the count rates obtained at other source depths and/or other densities.

One relatively simple yet accurate method of relating such counts is by using a two parameter least squares fit technique. The form of the function would be $$C = MC' + k$$

where C is the count rate of the first calibration block at a given source depth, C' is the count rate of a second different calibration block at the same source depth, and M and k are, respectively, the slope and y-intercept of the fitted line. By this method, three such fit equations could be developed at each of the source depth positions, each equation relating two count rates between two calibration blocks of different densities at any given source depth.

In practice, only two of the three aforementioned equations are needed at each depth because the third is redundant. The term k is found to be proportional to the count rate observed. Thus, a normalized version of the above equation is preferably utilized as follows:

$$C1 = M(C2) + k/C2$$

$$C3 = M'(C2) + k'/C2$$

where C2 is the counting rate observed on the single calibration block and C1 and C3 are the count rates calculated for two other calibration blocks of known densities. For a given calibration block, a large sampling of gauges previously calibrated by conventional methods is utilized in a linear least squares fit to the above equations to calculate appropriate values for M, M', k, k' for each particular set of calibration blocks to be utilized.

Utilizing the above-derived historical relationships, it is possible to calculate from a single experimental count taken at a predetermined depth, the expected calibration counting rates to be obtained for at least two other densities at the same depth. These three counting rates are then used in the normal fashion to obtain the calibration constants A, B, and C. This is referred to herein as the "one block" method.

It also possible to calculate from a single count at a known depth and known density, the expected counts at other depths in the same density block. This procedure, referred to herein as the "one point" calibration, uses historically derived relationships of the counts at the other depths.

Figure 2:
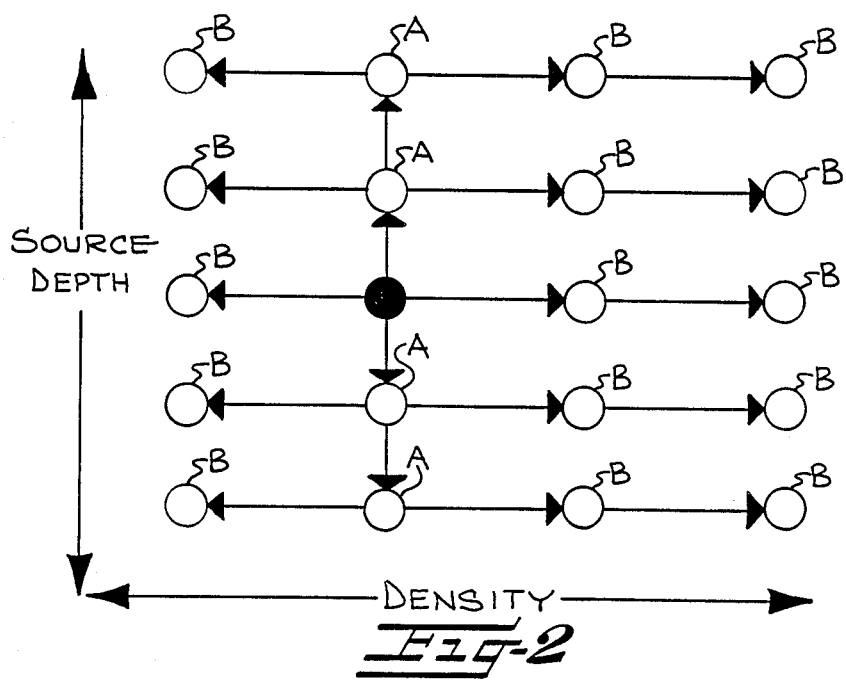
FIG. 2 is a schematic diagram illustrating the calibration procedure of the present invention.

The diagram of FIG. 2 schematically illustrates how the "one point" calibration procedure of the present invention can be utilized to determine, from a single experimental count, the calculated counts for each of a number of unknown points. In the diagram, the solid point represents the experimentally measured count, while the open points represent unknown points whose values are to be calculated. The points differ in density along the x axis and differ in source depth position along the y axis. While it is possible to start with any experimentally measured point, in practice it is preferred to utilize an experimental point of intermediate source depth position and intermediate density. By calculating up and down, utilizing the historically derived relationships between the count reading obtained from the calibration block to the count readings obtained from the same calibration block at other known source depth positions, it is possible to obtain values for other source depth positions at the same density. These calculations are represented in FIG. 2 by the vertical arrows and the thus calculated values are indicated by the reference character A. Now, given a known value at each source depth position, it is possible to calculate laterally to obtain values at the same source depth position for other densities. These calculations (represented by the horizontal arrows) are made using historically derived relationships between counts experimentally obtained from calibration blocks of other known densities at the same source depth positions. The thus derived values are indicated in FIG. 2 by the reference character B.

In the above example, the unknown points were determined by first calculating vertically to obtain values at the various source depth positions, and then calculating laterally to obtain values for other densities at the same source depth position. However, it will be recognized that in accordance with the present invention, the calculations can be carried out in any sequence, and in any direction, i.e. vertically, horizontally, or diagonally, once the relationships between the various points have been established In practice, we find it preferable to utilize the above procedure for determining most, but not all, of the unknown points required for calibration of a gauge. In particular, we find it preferable to use this procedure for calculating the intermediate source depth positions from a single point of intermediate density and source depth position, and to calibrate for the two extreme source depth positions, namely the backscatter position and the lowermost (deepest) source depth position, by taking a single experimental count reading at each such position, relying upon the "one block" method previously described to complete the calibration.

That which we claim is:

1. A method of calibrating a nuclear density gauge of the type having a gamma source which is positionable at several different source depth positions with respect to a detector to obtain the calibration constants A, B and C of the exponential equation $$CR = A\ exp(-BD) + C$$

where:
CR is the count ratio dervied by comparing an accumulated count from a test specimen to a standard count,
D is the density of the test specimen, and
A, B and C are calibration constants,
said method being characterized by reducing the number of experimental count readings required for calibration, and said method comprising the steps of:
(a) positioning the source at a predetermined source depth position on or in a calibration block of known density and obtaining a count by the detector for a predetermined period of time;
(b) calculating at least one additional count at another known density or another known source depth position using historically derived relationships between the count obtained from said calibration block of known density and the counts obtained from calibration blocks of other known densities and other known source depth positions; and
(c) utilizing the experimental count obtained from step (a) and the calculated count obtained from step (b), together with the respective densities, to derive a set of calibration constants A, B and C.

2. A method according to claim 1 wherein said step (b) comprises calculating counts for at least two other densities.

3. A method according to claim 1 wherein said step (b) comprises calculating counts for each of a plurality of different source depth positions in said calibration block of known density.

4. A method according to claim 1 wherein said step (b) comprises calculating counts for at least two other densities and for each of a plurality of different source depth positions at each density.

5. A method of calibrating a nuclear density gauge of the type having a gamma source which is positionable at several different source depth positions with respect to a detector to obtain the calibration constants A, B and C of the exponential equation $$CR = A\ exp(-BD) + C$$

where:
- CR is the count ratio derived by comparing an accumulated count from a test specimen to a standard count,
- D is the density of the test specimen, and
- A, B and C are calibration constants, said method being characterized by reducing the number of experimental count readings required for calibration, and said method comprising the steps of:

(a) positioning the source at a predetermined source depth position on or in a calibration block of known density and obtaining a count by the detector for a predetermined period of time;

(b) calculating the count at the corresponding source depth position for at least two other known densities using historically derived relationships between the count obtained from said calibration block of known density to the counts obtained from the calibration blocks of said at least two other known densities; and (c) fitting the thus derived counts to said exponential equation to obtain for said source depth position a set of calibration constants A, B and C.

6. A method according to claim 5 further comprising:

(d) calculating the count for at least one other source depth position using historically derived relationships between the count at said predetermined source depth position to the counts obtained from such other source depth positions; and (e) repeating steps (b) and (c) for each of the calculated counts obtained in step (d) to obtain a set of calibration constants for each of such other source depth positions.

* * * * *